United States Patent [19]

Hansen

[11] 4,411,622
[45] Oct. 25, 1983

[54] JAW HINGE-AXIS LOCATOR

[76] Inventor: Gorm P. Hansen, 1501 SE. 23rd Ave., Pompano Beach, Fla. 33062

[21] Appl. No.: 310,413

[22] Filed: Oct. 9, 1981

[51] Int. Cl.³ ............................................. A61C 19/04
[52] U.S. Cl. ...................................... 433/73; 433/72; 128/777
[58] Field of Search ....................... 433/73, 68, 69, 72, 433/229; 33/174 D; 128/774, 777, 782, 641

[56] References Cited

U.S. PATENT DOCUMENTS

| | | | |
|---|---|---|---|
| 1,497,259 | 6/1924 | Bonoff | 433/73 |
| 3,301,254 | 1/1967 | Schickedanz | 128/153 |
| 4,114,263 | 9/1978 | Szpur | 128/641 |
| 4,122,837 | 10/1978 | Leonard | 128/774 |
| 4,210,245 | 7/1980 | Dodge | 128/153 |

*Primary Examiner*—John J. Wilson
*Attorney, Agent, or Firm*—Diller, Ramik & Wight

[57] ABSTRACT

A jaw hinge-axis locating device for securing a dental face-bow of the type having hinge pointers to the face of a dental patient with the hinge pointers of the face-bow in axial alignment with the patient's jaw hinge axis, the device includes a pliable base member which is adapted to be adhesively secured to a patient's face over one of his jaw hinge condyles, a receptacle disposed on the base member which is adapted securely to receive a hinge pointer of a face-bow with the receptacle in alignment with a patient's jaw hinge-axis thereby to locate and maintain a hinge pointer of a face-bow in alignment with the jaw hinge-axis of a patient.

9 Claims, 5 Drawing Figures

JAW HINGE-AXIS LOCATOR

BACKGROUND OF THE INVENTION

In the dental art, it is often necessary for a dentist to obtain casts of a dental patient's teeth. These casts, typically, are obtained by having a patient bite down on a bite-fork which contains a molding medium. To obtain these casts, a dentist ordinarily places a face-bow, which has a bite-fork secured thereto, on the head of a dental patient. This face-bow, generally, consists of an arcurate member which spans across the front of a patient's face from one side to the other and has a pair of opposed inwardly directed hinge pointers which are adapted to be secured to the patient's face in alignment with his jaw hinge-axis. The aforementioned bite-fork is generally centrally disposed on the arcurate member of the face-bow so that the dentist can make a cast of the patient's teeth and at the same time be able to ascertain the space relationship between the patient's teeth and his jaw hinge-axis.

The task of placing the face-bow in proper alignment with the patient's jaw hinge-axis often proves to be quite awkward, as the face-bow must be rigidly secured to the patient's face with the hinge pointers thereof being disposed in overlying registry with the patient's jaw hinge condyles. Generally, the dentist locates the patient's jaw hinge condyles and marks the patient's skin indicating the location of same. The dentist then places the face-bow on the patient's head making sure that each hinge pointer is located over the marks previously placed on the patient's face. However, this often requires the use of an assistant, as one hand is required to hold the face-bow and another hand is required for each hinge pointers in order to place them in proper position. This procedure is further complicated by the fact that the face-bow must be rigidly secured to the patient's face with sufficient pressure to prevent the hinge pointers from slipping away from their requisite locations. A further complication, of course, is that the face-bow cannot be placed so tightly on the patient's face as to cause him discomfort. In order to prevent discomfort to the patient, dentists have, in the past, used various head cap apparatuses which consist of a cap worn by the patient having a pair of depending flag portions each of which is adapted to be disposed between a patient's jaw hinge condyle and the hinge pointer. The use of such head cap apparatuses further complicates this procedure as the dentist and his assistant must make certain that each of the flag portions, as well as the hinge pointers, is in proper alignment with the patient's jaw hinge-axis.

SUMMARY OF THE INVENTION

The present invention pertains to a jaw hinge-axis locator which is adapted to be adhesively secured to the side of a patient's face so that a dentist can secure a face-bow to a patient's face completely unassisted. The jaw hinge-axis locating device or locator of the present invention comprises, in general, a pliable and transparent disc which the dentist adhesively secured to the side of a patient's face over the patient's jaw hinge condyle, and a receptacle which extends outwardly from the disc and is adapted to be disposed in alignment with the patient's jaw hinge-axis. The receptacle of the locating device is adapted to receive therewithin a hinge pointer of a face-bow. In this manner the procedure of placing a face-bow on a dental patient's face is much simplified as the dentist merely has to secure the hinge-axis locator of the present invention over each of the patient's jaw hinge condyles, with the receptacles thereof in axial alignment with the patient's jaw hinge-axis, and then place the hinge pointers of the face-bow into the receptacles of the hinge-axis locators. This allows the dentist to place a face-bow on a patient's face unassisted, as he can place one hinge pointer in one receptacle and then place the other hinge pointer within its associated receptacle without having to worry that the first hinge pointer may have slipped away from its mark. In this way, the dentist can place each hinge pointer within its associated receptacle independently of the other for he is assured that each hinge pointer will remain where he had originally put it. Also, by using a hinge locator of the present invention over each of the patient's jaw hinge condyles, the dentist can forego the use of head caps or the like, as the face-bow is maintained on the patient's face by the hinge locators and not by a clamping force against the side of the patient's head. Of course, if the face-bow is not held on the patient's face by a clamping force, the dentist does not have to concern himself with possible discomfort to the patient.

BRIEF DESCRIPTION OF THE DRAWING FIGURES

DETAILED DESCRIPTION OF THE DRAWING FIGURES

Figure 1:
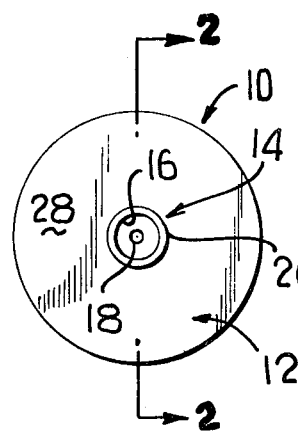
FIG. 1 is a top plan view of the hinge-axis locating device of the present invention.

Referring to FIG. 1, a hinge-axis locating device of the present invention is generally indicated by the reference character 10. The hinge-axis locating device or locator 10 comprises a planar pliable card, disc or base member 12, preferably of circular configuration, and a generally centrally disposed locating means 14 defined by receptacles 16, 18.

Figure 2:
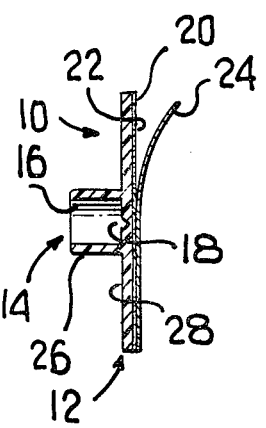
FIG. 2 is a sectional view taken generally along line 2—2 of FIG. 1.

In FIG. 2, the base member 12 has a pressure-sensitive adhesive 20 disposed on one surface 22 thereof. The device 10 is also provided with a removable backing 24 which is initially disposed over the adhesive layer 20 in order to prevent the device 10 from becoming adhesively secured to foreign matter or from being adhered to a patient's face prematurely. The receptacle 16 of the locating means 14 is defined by a cylindrical wall 26 which extends transversely outwardly from another surface 28 of the device 10, and the receptacle 18 is defined by a conical indentation which extends transversely inwardly from the surface 28.

Figure 3:
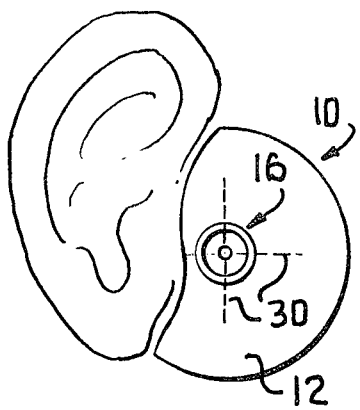
FIG. 3 is a top plan view of the preferred embodiment of the present invention shown in situ over a patient's jaw hinge condyles.

In a preferred embodiment of the invention, as illustrated in FIG. 3, the base member 12 of the device 10 is formed from transparent, thin, pliable and severable (easily cut) plastic material. Due to the transparency of the device 10, the dentist is facilitated in placing the generally centrally disposed locating means 16 in proper axial alignment with the patient's jaw hinge-axis. As noted hereinbefore, it is standard procedure for the dentist to mark the patient's face in order to indicate the location of the patient's jaw hinge-axis, as noted by the phantom lines 30. Therefore, when the dentist proceeds to apply the device 10 to the patient's face, he merely has to view the marks 30 through the transparent locator 10 in order to assure that the locating means 16 is properly disposed in axial alignment with the patient's jaw hinge-axis. Also, due to the severability of the base member 12, the dentist can cut away a portion thereof in order to preclude any obstruction of the placement of the device 10 by facial features of the patient, e.g., a patient's ear. In this manner, the dentist can cut the normally circular base member 12 of the locating device 10 to fit the patient's face and then remove the removable backing 24 (FIG. 2) and apply the device 10 to the patient's face in proper registry over the patient's jaw hinge condyle.

Figure 4:
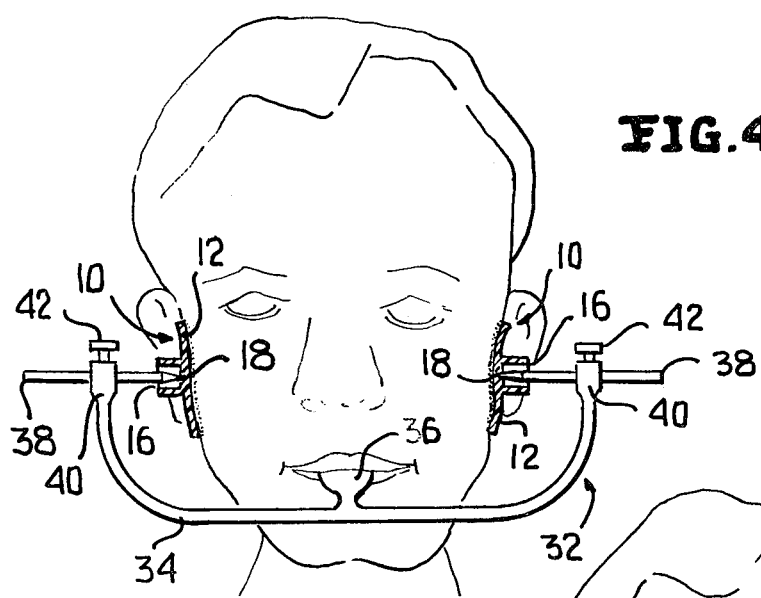
FIG. 4 is a front view of a face-bow with the hinge pointers thereof being secured to a patient's face by a pair of hinge locators of the present invention.

FIG. 4 is an illustration of the patient having a face-bow 32 secured to his face by a pair of the locating devices 10 of the present invention. The face-bow 32 generally comprises a generally arcuate bow member 34 which spans across the front of a patient's face from one side to the other. The face-bow 32 is provided with a suitable bite-fork 36 which is engaged by a patient's mouth, and a pair of hinge pointers 38 each of which is adapted to be engaged by the locating means 16 of its associated hinge-axis locator 10. As is conventional, each hinge pointer 38 is adapted to extend through an associated apertured end portion 40 of the face-bow 32 and is secured thereto by a set-screw 42 or any other suitable means. This allows each of the hinge pointers 38 to be axially adjustable independently of the other. In this way, the dentist can place one hinge pointer 38 within its associated locating means 16 and then adjust the axial extent of the other in order to have it securely received within its associated locating means 16. The hinge pointers 38 of FIG. 4 are of the pin-point type and, therefore, each is received within the conical indentation or receptacle 18 thereby to secure the face-bow 32 to the patient's face. Due to the pliability of the base member 12, each of the devices 10 is adapted to conform to the contours of the patient's face.

Figure 5:
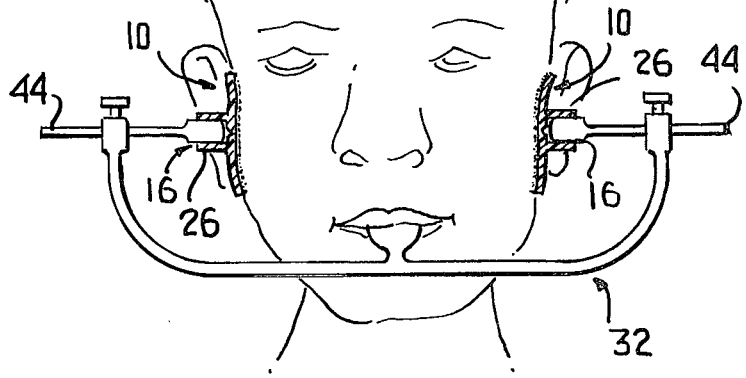
FIG. 5 is a front view of a face-bow having a different type of hinge pointers which are secure to a patient's face by a pair of the devices of the present invention.

FIG. 5 is a further view of the face-bow 32 which is secured to a patient's face by a pair of hinge-axis locators 10 via associated hinge pointers 44. The hinge pointers 44 of FIG. 5 are of the cup type and, therefore, each is secured within the confines of the cylindrical wall 26 of its associated receptacle 16. In this manner, the hinge-axis locator 10 is adapted to receive both hinge pointers of the pin-point type and of the cup type. Accordingly, since these types of hinge pointers are the most prevalently used, the present invention is particularly suitable for use with conventionally utilized face-bows.

Therefore, the device 10 of the present invention obviates a dentist's need for assistance when placing a face-bow on a dental patient, as he will not need an extra pair of hands, so to speak, in order to retain each of the hinge pointers in proper disposition over a patient's jaw hinge condyles, since this is the function performed by the locating means 16 of the present invention. Further, the use of the present invention will preclude any discomfort to the patient as it obviates the present necessity of retaining a face-bow on a patient's face through a clamping force which relies upon frictional engagement of the hinge pointers against the side of a patient's face.

It is to be noted that the illustrations and descriptions contained herein are intended to allow one of ordinary skill in this art to practice the present invention and not to limit the scope of same any further than as required by the appending claims.

I claim:

1. A device for securing a dental face-bow of the type having hinge pointers to the face of a dental patient with the hinge pointers of the face-bow in axial alignment with the patient's jaw hinge-axis, said device comprising in combination:

a base member adapted to be adhesively secured to a patient's face over a jaw hinge condyle;

means disposed on said base member for receivingly locating a hinge pointer of a face-bow therewithin in axial alignment with a patient's jaw hinge axis; and said base member being a generally pliable and planar card having an adhesive disposed on one surface thereof.

2. The device as defined in claim 1 wherein said base member is of a circular configuration.

3. The device as defined in claim 1 wherein said locating means comprises a central, conical depression extending transversely inwardly from another surface of said base member, thereby to receive a hinge pointer having a pin-point tip.

4. The device as defined in claim 1 wherein said locating means comprises a centrally disposed cylindrical wall extending transversely outwardly from said another surface of said base member, thereby to receive a hinge pointer having a blunt tip.

5. The device as defined in claim 1 wherein said locating means comprises a centrally disposed cylindrical wall extending transversely outwardly, and a central, conical depression extending transversely inwardly, from said another surface of said base member, thereby to receive a hinge pointer having a blunt tip or a pin-point tip.

6. The device as defined in claim 5 wherein said base member is constructed of a transparent material thereby to facilitate the placement of same over a patient's jaw condyle.

7. The device as defined in claim 6 wherein said base member is constructed of severable material thereby permitting a portion thereof to be cut away to allow same to conform to features of a patient's face.

8. The device as defined in claim 7 wherein said base member is initially provided with a removable backing covering said adhesive thereby to preclude premature or inappropriate adhesion.

9. The device as defined in claim 8 wherein said base member is of a circular configuration.

* * * * *